United States Patent [19]

Wason

[11] 3,967,563

[45] July 6, 1976

[54] PROCESS FOR PRODUCING PRECIPITATED THICKENER SILICA

[75] Inventor: Satish K. Wason, Havre de Grace, Md.

[73] Assignee: J. M. Huber Corporation, Locust, N.J.

[22] Filed: Aug. 20, 1975

[21] Appl. No.: 606,035

Related U.S. Application Data

[63] Continuation of Ser. No. 402,927, Oct. 3, 1973.

[52] U.S. Cl. .............................. 106/288 B; 106/309; 423/339
[51] Int. Cl.² ............................................ C09C 1/28
[58] Field of Search ...................... 106/288 B, 309; 423/335, 339

[56] References Cited
UNITED STATES PATENTS 3,250,594    5/1966    Burke.............................. 106/288 B Primary Examiner—Helen M. McCarthy
Assistant Examiner—J. V. Howard
Attorney, Agent, or Firm—Harold H. Flanders; Robert L. Price

[57] ABSTRACT

Precipitated silicas having very high structure as defined by the ability of the silica material to hold water in its wet cake, high oil absorption, and very high surface area can be produced by controlling the rate of acidulation during their production and maintaining the same at a very low rate during the course of the addition of acid to the solution of alkali metal silicate. The control of the index of refraction of the silica so produced is achieved by introduction of controlled amounts of adduct material such as aluminum sulfate to the acid prior to its introduction to the silicate solution.

6 Claims, No Drawings

PROCESS FOR PRODUCING PRECIPITATED THICKENER SILICA

This is a continuation of application Ser. No. 402,927, filed Oct. 3, 1973.

The present invention relates to the novel silicic acid or silica products and, more particularly, to a method for producing synthetic precipitated silicas having new and unique properties.

As known in the art, commercially available silicas can broadly be divided into two basic categories. These categories are those produced from a liquid phase and those from a vapor phase process.

Liquid phase silicas include precipitated silicas produced by acidulating an alkali metal silicate with an acid such as sulfuric acid. Further liquid phase silicas are silica gels and colloidal silicas. Examples of prior techniques involving the acidulation of a silicate solution to produce precipitated silicas are disclosed in U.S. Pat. Nos. 3,110,606 and 3,582,379.

Vapor process silicas, also called fumed and pyrogenic silicas, are prepared by reacting silicon tetrachloride vapor with an oxygen-hydrogen gas at high temperatures to produce silica and hydrogen chloride. Pyrogenic silicas have high external surface areas and differ from other silicas (e.g., gels, precipitated silicas, etc.) prepared from the liquuid phase process.

While precipitated silicas have been used in many applications, various properties thereof (such as low abrasiveness) render them unsuitable for many uses. For example, it is known that conventional synthetic precipitated silicas are unsuitable as polishing and abrasive agents in toothpaste composition. See U.S. Pat No. 3,250,680 and German Pat. No. 974,958. U.S. Pat. No. 3,538,230 specifically discloses that known amorphous silicas, such as precipitated silicas, pyrogenic silicas and aerogels are unsuitable for dentifrice use because of their initial small particle size and because of the ease in which they break down into smaller particle sizes.

In recent years and to further expand the utility of precipitated silicas, prior art workers have developed new techniques for producing silica having new and unique properties; e.g., render them particularly suitable for use in toothpaste compositions and as a replacement for phosphate polishing agents.

Thus, there is disclosed in U.S. Ser. No. 285,966, filed Sept. 15, 1972, process for producing precipitated silicas which may be used as an abrasive or polishing agent in toothpaste wherein a salt or electrolyte is employed to pre-polymerize the alkali metal silicate prior to its acidulation with an acid.

In accordance with a further innovation, there is disclosed in U.S. Ser. No. 403,129, now abandoned, and refiled as Ser. No. 606,036, filed Aug. 20, 1975 (Docket No. 72-211) a process for producing precipitated silica that have high abrasiveness and a relative cleaning ability equivalent to high grade phosphates used as polishing agents in toothpastes. In accordance with teaching of this patent application, the silica products are produced by the simultaneous introduction of a solution of an alkali metal silicate and an acid into an aqueous receiving medium (i.e., water) and maintaining the pH of the aqueous receiving medium constant during the precipitation thereof.

In summary, the present invention provides a further improvement in the production of precipitated silicas involving the acidulation of an alkali metal silicate with an acid. In its broadest aspects, the invention is based on the discovery that silica having improved properties and characteristics can be produced by carefully controlling the rate of the acidulation. More specifically, it has been found that silica products having very high structure (as defined hereinafter), high oil absorption and a very high surface area can be produced by controlling the acidulation and maintaining same at a very low rate during the course of its (the acid) addition to the solution of the alkali metal silicate. In this manner, the precipitation is effected under a homogeneous environment and such that the ultimate particle size is controlled. The resulting product has the above noted improved characteristics which render the product particularly suitable for use as a thickening agent in toothpaste formulations, as a flatting agent in paints and varnishes and the like.

In this regard and before turning to the more precise details of the invention, precipitated silicas have not been used as thickening and gelling agents in toothpaste. In general when phosphates are employed as the polishing or abrasive agent, a thickening agent, such as gum tragacanth, has been employed. See U.S. Pat. No. 2,588,992.

In more recent years, the use of precipitated silicas (such as disclosed in the aforementioned patent applications) as polishing or abrasive agents has created the need for, and the general use of, siliceous materials as thickeners. Specific examples of siliceous thickeners or gelling agents are disclosed in U.S. Pat. No. 3,538,230. The thickeners disclosed in the latter include "Cab-O-Sil" (pyrogenic silica) and "Syloid 244" (aerogel).

Thus, an object of the present invention is to provide a process for producing a finely divided precipitated silica that may be employed as a thickening and/or gelling agent for dentifrices.

The products of the invention, as will be described in detail hereinafter, have a controlled refractive index, a very high structure and may also be used as reinforcing agents, flattening agents in paints and varnishes, as flow conditioner and the like.

The manner in which the foregoing and other objects are achieved in accordance with the present invention will be better understood in view of the following detailed description which discloses particularly advantageous method and composition embodiments for illustrative purposes.

In this regard, in the practice of the process of the invention, a solution of an alkali metal silicate is first charged to a reaction vessel (equipped with suitable heating and agitation equipment) with the silicate solution then being heated to a temperature in the range of from 150° to 170°F, preferably in the range of from about 160° to 165°F. The silicate solution may, of course, be prepared in the reaction vessel itself.

As used herein, the term "alkali metal silicate" includes all the common forms of alkali silicates, as for example metasilicate, disilicates and the like. Water-soluble potassium silicates and sodium silicates are particularly advantageous, with the latter being preferred.

In general, sodium silicates are effective in any composition in which the weight ratio of $SiO_2$ to $Na_2O$ is from about 1.0 to 4.0. However, particularly advantageous and thus preferred results are obtained if the $SiO_2/Na_2O$ weight ratio is in the range of from about 2.5 to 3.3.

After the solution has been heated to the above-noted temperature, the acidulating agent or acid is added at a very slow rate and in the range of from 200 to 350 ml/min. In conventional processes involving the acidulation of a silicate, the rates of addition have in general been very high and on the order of 500 ml/min. In the present invention the rate of addition must not exceed (at any stage of acidulation) a rate in excess of or above about 350 ml/min.

The acid is preferably a strong mineral acid, such as sulfuric acid, nitric acid, and hydrochloric acid. However, other acids including organic acids or salts thereof (for example, acetic acid, formic acid, carbonic acid, ammonium carbonate, etc.) can be employed.

The acid is preferably added as a dilute solution thereof with preferred results being obtained if the acidic solution comprises from about 8 to 25% by weight acid, based on the total weight of the solution.

Particularly advantageous results are obtained if the silicate concentration of the initial silicate solution is on the order of from about 10 to 20% by weight, based on a total weight of the silicate solution.

As will be seen from the above, the starting materials include the alkali metal silicate and the acid. Significant process variables include the $SiO_2/Na_2O$ weight ratio, the reaction temperature and the rate of the acid addition to the solution of the alkali silicate.

In this regard, it has also been found that the refractive index of the product (as well as the other aforementioned properties) can be carefully controlled and maintained if an adduct material, such as aluminum sulfate, is premixed with the acid prior to its introduction into the silicate solution. Thus, prior to the acidulation, the aluminum sulfate (preferably as a solution thereof) is premixed with the acid such that its concentration is on the order of about 3 to 10% aluminum sulfate based on total weight of the acid. While the adduct material is preferably a water-soluble aluminum salt, such as aluminum sulfate, other salts such as magnesium sulfate may be employed. As indicated, the adduct is premixed with the acid and the acid/metal salt mixture is then used for acidulating the aqueous solution of the alkali metal silicate.

As indicated above, the products of the invention have a very high structure. Thus at this point, it may be noted that as used herein the term "structure" is intended to include, and is defined as, the ability of a silica material to hold water in its wet cake; i.e., after the precipitate has been filtered. Commercially available precipitated silicas hold a high percentage of water (i.e., in the neighborhood of 75 to 85%) and are known and referred to as high structure silicas. Materials holding water in a range of 65 to 75% are generally referred to as medium structure silicas. Silicas having wet cake moistures in excess of 85% and up to 95% and higher are referred to as very high structure silicas.

The present invention is directed to the production of very high structure, thickener silicas produced under carefully controlled acidulation conditions.

As previously noted, it is well known in the art that precipitated silicas are prepared by acidulating an aqueous alkali metal silicate with a suitable acidulating agent until a final pH of from about 5.6 to 6.0 is obtained. The silica precipitate is then filtered, washed free of salts, dried, and milled to desired degree of fineness.

The objects of the present invention are to provide an improved process for the preparation of very high structure, thickener silicas; to provide a process for controlling the relative sizes and uniformity of the primary particles; and to provide unique silicas having improved functionality in toothpaste compositions and other use areas.

In this regard and turning now to further details of the invention, commercially available sodium silicate solutions may be represented by the formula $Na_2O \cdot xSO_2$, wherein $x$ stands for the weight ratios of $SiO_2/Na_2O$. Since the molecular weights of $Na_2O$ and $SiO_2$ are substantially the same, it is common practice to use weight ratios for sodium silicates. Water glass is the most commonly used silicate for preparing silicic acid pigments. This product has a weight ratio of 3.22 which means that it has 3.22 parts of $SiO_2$ and one part alkali; i.e., $Na_2O$.

In the prior art, it has been customary to acidulate a sodium silicate wherein the value of $x$ was in the range of from about 3.0 to 3.4. In this prior practice, the acid was merely introduced in the sodium silicates solution until the desired final pH was obtained, with the product then being recovered using the conventional procedures.

In the present invention, the acidulation is very carefully controlled, particularly at the outset of the reaction and at that point at which the precipitation initially occurs; i.e., wherein the value of $x$ is approximately 4.2.

The invention will be further illustrated by the following examples which set forth particularly advantageous method embodiments. While the examples serve to illustrate the present invention, they are not intended to limit it thereto.

EXAMPLE 1

In this experiment 10 gallons of a sodium silicate solution having an $SiO_2/Na_2O$ weight ratio of 2.6 was added to a stirred reaction vessel and the solution was heated to 165°F. The concentration of the silicate solution was 13.3%. Sulfuric acid of 11.4% concentration and aluminum sulfate solution (1.4 lbs/gal.) were premixed in the ratio of 100 to 7 by volume. This mixed acidulating agent was then added very slowly to the reactor at a rate of 300 ml/min. until a final pH of 5.9 was obtained. The product of this example had very high structure, a wet cake moisture of 88%, an oil absorption of 240 cc/100 g and a surface area of 250 $m^2/g$.

EXAMPLE 2

The procedure of Example 1 was repeated except that the rate of addition of the premixed acidulating agent was 250 ml/min. The product of this example had very high structure, a wet cake moisture of 87%, an oil absorption of 230 cc/100 g and a surface area of 275 $m^2/g$.

EXAMPLE 3

The procedure of Example 1 was repeated except that the rate of addition of the acidulating agent was 275 ml/min. The product of this example had very high structure, a wet cake moisture of 86%, an oil absorption of 220 cc/100 g and a surface area of 265 $m^2/g$.

EXAMPLE 4

The procedure of Example 1 was repeated except that the rate of acidulating agent was maintained at 225 ml/min. up to the initiation of precipitation at an $x$ value of 4.2. The product of this example had very high structure, a wet cake moisture of 89%, an oil absorption of 250 cc/100 g and a surface area of 280 m²/g.

EXAMPLE 5

As a control example, 10 gallons of a sodium silicate solution having an $SiO_2/Na_2O$ weight ratio of 2.6 was added to a stirred reaction vessel and the solution was heated to 165°F. The concentration of the silicate solution was 13.3% Sulfuric acid of 11.4% concentration was added to the reactor at a rate of 500 ml/min. until a final pH of 5.9 was obtained. The product of this control example was only of high structure with a wet cake moisture of 84%, an oil absorption of 180 cc/100 g and a surface area of 150 m²/g.

As the above examples illustrate, the production of silica of very high structure is made possible by a carefully controlled acidulation to and about the point of initial precipitation at an $x$ value of 4.2 in the case of sodium silicate of weight ratio ($x$ value) $SiO_2/Na_2O$ of 2.6 and 13.3% concentration. By controlling the acidulation to and about the $x$ value of 4.2 for as long a time as practically possible, it is possible to control the ultimate silica particles and precipitate them under homogeneous environments with controlled micelle formation during the precipitation process. This controlled process then yields a silica of improved characteristics and functionality when compared with silica produced by prior art processes.

When the findings illustrated by the above examples are correlated with related findings, it is found possible to note that mol ratio and weight ratio of $SiO_2/M_2O$, where M is an alkali metal such as sodium, potassium and the like, is inversely proportional to the number of mols of hydrogen ions provided by the acidulating agent per unit time to provide the controlled micelle formation during the precipitation of the silica required in a process in accord with the present invention.

For the above examples employing a sodium silicate of weight ratio ($x$ value) $SiO_2/Na_2O$ of 2.6, the preferred rate of acidulation is from 200 to 350 ml/min. or from approximately 0.4 mol to 0.8 mol of hydrogen ions per minute.

In general, the desired rate of acidulation of an alkali metal silicate of mol (or weight) ratio $x = SiO_2/M_2O$, where M is an alkali metal, is from $[H^+]/x$ to $2[H^+]/x$, where $[H^+]$ is the mol concentration of hydrogen ions to be added per minute.

The silicas of the present invention was produced in two 1500 pound lots to confirm the data and effectiveness of the product of Examples 1 – 4. These runs resulted in materials with the following properties:

| Run and Product A: | Oil Absorption: | 237 cc/100 g |
|---|---|---|
| | Surface Area: | 308 m²/g |
| Run and Product B: | Oil Absorption: | 222 cc/100 g |
| | Surface Area: | 259 m²/g |

The surface area of Product A was higher than that of Product B because it was finished at a lower final pH than was Product B.

The thickening efficiency of Products A and B was compared in typical humectant systems used in dentifrices.

Two humectant systems were used: one designated "C" comprising a 70% sorbitol solution sold as SORBO by Atlas Chemical, Inc., Wilmington, Delaware, and another designated "D" comprising a blend of 45 parts of a 70% sorbitol solution and 15 parts of a 95% glycerol solution.

Products A and B were dispersed by stirring in a known weight of each of humectants "C" and "D" until a free flowing powder was obtained. Silica of Example 5 was also dispersed in humectants "C" and "D" for comparison.

The control silica retained a maximum of 280% of "C" and 270% of "D." Product A retained a maximum of 300% of "C" and 296% of "D." Product B retained a maximum of 294% of "C" and 296% of "D."

As can be seen, the silicas of the present invention have superior thickening or drying-up capacity for typical humectants to the prior art silica.

Thus, the very high structure silicas of the present invention can be used as gelling and thickening agents in a variety of dentifrice and toothpaste compositions.

Silicas of the present invention can also be used as reinforcing agents, flatting agents in paint and varnished, as a carrier, as flow conditioners, as a liquid drying agent and the like.

For flatting application, 10 grams of silica (which was airmilled) of the instant invention was mixed with 350 grams of the nitrocellulose lacquer (conforming to Military Specification MIL-L-10287A - amendment 2, Type II, of issue Aug. 27, 1959) and mixed for 3 minutes using the low speed setting of the Hamilton-Beach No. 30 mixmaster. The lacquer containing dispersed silica was tested for Hegman fineness of grind (5.50) and cleanliness of grind.

The lacquer containing dispersed silica was mixed with no lacquer and additional lacquer to prepare stock solution containing 10%, 3.5%, and 1.75% by weight of vehicle solids. A draw down of various stock solutions (containing 10%, 3.5% and 1.75% silica in lacquer) was made on carrara glass using a No. 34 wire wound coatings application rod. Carrara glass draw downs were allowed to dry for 45 minutes under dustfree conditions. Using the above method, draw downs were also made from stock solutions containing the silica developed via the prior art processes.

Using the Gardner multi-angle gloss meter, the gloss and sheen values of the various draw downs were measured at 60° and 85°, respectively. These values were compared with measured values obtained when a prior art silica was dispersed in the lacquer.

Silicas of the present invention result in cleaner Hegman grinds and exhibit better clarity when dispersed in the lacquer. The better clarity is attributed to the fact that the silicas of the present invention are of uniform particle sizes and favorable structures.

Flatting data below suggests that the novel silicas of the present invention exhibit lower gloss and sheen values than the control. Lower gloss and sheen values are preferred and advantageous for paint flatting application.

| FLATTING DATA | | | | | | |
|---|---|---|---|---|---|---|
| | 60° Gloss | | | 85° Sheen | | |
| | 10% | 3.5% | 1.75% | 10% | 3.5% | 1.75% |
| Silica via Example 1 | 8 | 29 | 44 | 28 | 61 | 74 |
| Silica via Example 5 (control) | 10 | 38 | 54 | 37 | 72 | 82 |

Although preferred embodiments of the present invention are described in detail above, the illustrative description is not intended to limit or restrict the invention disclosed to those skilled in the art and the invention is thus declared to cover all changes and modifications of the above disclosure which do not constitute departures from the spirit and scope of the claimed invention.

What is claimed is:

1. A method for producing a unique, amorphous, precipitated silica having very high structure, wet cake moisture in excess of 85%, an oil absorption in excess of 200 cc/100g., a surface area in excess of 250 m²/g, and having improved chemical and physical properties, said method comprising the steps of:
   a. providing an aqueous reaction medium containing 10–20% by weight of an alkali metal silicate, said alkali metal silicate having an $SiO_2/M_2O$ weight ratio, $x$, ranging from 1.0 to 4.0, where M is an alkali metal;
   b. heating said reaction medium at a temperature of from 150° to 170°F; and
   c. adding to said aqueous reaction medium an acidulating agent comprising a mineral acid at a constant rate ranging from $1x$ to $2/x$ mols of hydrogen ions per minute.

2. A method according to claim 1 wherein the reaction temperature is from 160° to 165°F, said alkali metal silicate is sodium silicate of weight ratio, $x$, from 2.4 to 3.3, said acidulating agent is a dilute solution of from 8 to 25% by weight of a strong mineral acid, and said rate of acid addition is from 0.3 to 0.8 mol of hydrogen ions per minute.

3. A method according to claim 2 wherein said reaction temperature is 165°F, said alkali metal silicate is sodium silicate of weight ratio, $x$, 2.5±1, and said acidulating agent is sulfuric acid added at a rate of from 200 to 350 ml/minute and from 0.4 to 0.8 mol of hydrogen ions per minute.

4. A method according to claim 1 further comprising adding an adduct of from 3 to 10% by weight of a water-soluble aluminum salt to said acidulating agent prior to its introduction to said reaction medium.

5. The method of claim 4 wherein said aluminum salt is aluminum sulfate.

6. A composition of matter comprising an amorphous, finely-divided precipitated silica having a wet cake moisture content of greater than about 85%; an oil absorption greater than about 200 cc/100g; and a surface area greater than about 250 m²/g.

* * * * *

UNITED STATES PATENT AND TRADEMARK OFFICE
CERTIFICATE OF CORRECTION

PATENT NO. : 3,967,563
DATED : July 6, 1976
INVENTOR(S) : Satish K. Wason

It is certified that error appears in the above-identified patent and that said Letters Patent are hereby corrected as shown below:

Column 1, line 27, "liquuid" should be -- liquid --.

Column 7, line 24, following "ranging from", "1x" should be -- 1/x --.

Signed and Sealed this

Third Day of April 1979

[SEAL]

Attest:

RUTH C. MASON
Attesting Officer

DONALD W. BANNER
Commissioner of Patents and Trademarks